United States Patent [19]

Selker et al.

[11] Patent Number: 4,998,535
[45] Date of Patent: Mar. 12, 1991

[54] THROMBOLYSIS PREDICTIVE INSTRUMENT

[75] Inventors: Harry P. Selker, Wellesley, Mass.; Galen S. Wagner, Durham, N.C.; W. Douglas Weaver, Seattle, Wash.; Robert M. Califf, Durham, N.C.

[73] Assignees: Univ. of Washington New England Medical Center Hospitals, Inc., Seattle, Wash.; Duke University, Durham, N.C.

[21] Appl. No.: 403,129

[22] Filed: Sep. 5, 1989

[51] Int. Cl.⁵ .................................................. A61B 5/04
[52] U.S. Cl. ...................................... 128/696; 128/702
[58] Field of Search .................. 128/695, 696, 702, 703, 128/704, 705

[56] References Cited

U.S. PATENT DOCUMENTS

| | | | |
|---|---|---|---|
| 4,181,135 | 1/1980 | Andresen et al. | 128/704 |
| 4,457,315 | 7/1984 | Bennish | 128/704 |
| 4,664,125 | 5/1987 | Pinto | 128/695 |
| 4,679,144 | 7/1987 | Cox et al. | 364/417 |
| 4,680,708 | 7/1987 | Ambos et al. | 364/417 |
| 4,754,762 | 7/1988 | Stuchl | 128/696 |

OTHER PUBLICATIONS

Cardiology Update, Reviews for Physicians, 1986 Edition, by Elliot Rapaport, "Thrombolysis in Acute Myocardial Infarction", by Sherman et al., pp. 117-135.

Michael W. Pozen et al., "A Predictive Instrument to Improve Coronary-Care-Unit Admission Practices in Acute Ischemic Heart Disease", The New England Journal of Medicine, 310:1273-1278, 1984.

Primary Examiner—Francis Jaworski
Assistant Examiner—George Manuel
Attorney, Agent, or Firm—Fish & Richardson

[57] ABSTRACT

An instrument for predicting the benefit of using thrombolytic therapy to treat a patient with a heart condition including a first input port for receiving inputs derived from electrocardiograph measurements of the patient's condition, and a processor for computing an estimate of said benefit based upon the electrocardiograph-derived inputs.

19 Claims, 3 Drawing Sheets

| coefficient | value | variable | description of variable |
|---|---|---|---|
| $b_0$ | -2.893 | (intercept value) | |
| $b_1$ | -1.694 | (SEX) | 1 if patient is male<br>0 otherwise |
| $b_2$ | 0.560 | (HMXI) | 1 if previous history of MI<br>0 otherwise |
| $b_3$ | 2.358 | (A23) | 1 if age > 65 years old<br>0 otherwise |
| $b_4$ | 2.519 | (K34) | 1 for Killip class 2,3 or 4<br>0 otherwise |
| $b_5$ | -0.366 | (T1) | 1 if 0-3 hours since onset<br>0 otherwise |
| $b_6$ | 0.612 | (S1) | 1 if anterior MI<br>0 otherwise |
| $b_7$ | -1.030 | (S2) | 1 if inferior MI<br>0 otherwise |
| $c_0$ | -0.581 | (T) | 1 if TT is used<br>0 otherwise |
| $c_1$ | 0.478 | T2) | 1 if > 6 hours since onset<br>0 otherwise |
| $c_2$ | 0.400 | (HXMI) | 1 if previous history of MI<br>0 otherwise |

FIG. 3

THROMBOLYSIS PREDICTIVE INSTRUMENT

The Government has rights in this invention pursuant to Contract/Grant No. 5 R01 HS06208 awarded by the National Institutes of Health.

BACKGROUND OF THE INVENTION

The invention relates to a computer-assisted electrocardiograph.

Thrombolytic therapy (TT), if given very early in the course of certain types of acute myocardial infarction (AMI), may be the most effective single therapy devised thus far for AMI. Controlled clinical trials have now well-established that if given early enough, TT's impact on acute mortality may approach, or even exceed, a 50% reduction. Moreover, benefits have also been documented in increased patency of infarct-related coronary arteries; improved left ventricular ejection fraction (LVEF) (i.e. cardiac function); and, as would be expected in conjunction with greater LVEF, improved long-term mortality.

If patient outcomes in the general clinical use of TT reach this level of performance, the national impact will be substantial. Even if emergency medical service (EMS) does not significantly improve its capture of the current large number of AMIs that never benefit from acute hospital care, the savings in lives would still be in the thousands. Given the more than 250,000 AMI patients hospitalized in this country every year, a drop in acute mortality from the typical 15% to 7.5% would save nearly 20,000 lives annually, not including the additional improved long-term survival also accrued by TT.

However there are reasons for limiting unrestrained use of TT. The complications can be serious, including stroke, hemorrhage, and other problems. If TT were to be used on a widespread, indiscriminate basis, the impact from these complications could be significant. In addition, a single administration of current state-of-the-art drugs for TT (e.g., tissue-type plasminogen activator: tPA) is very expensive and once given, its use leads to yet more expensive intensive care hospitalization, and either immediate or follow-up invasive tests and/or treatment, which otherwise would be less likely done. Thus, the financial impact of the widespread use of TT for acute care alone, without accounting for related additional coronary bypass surgery, may be over one billion dollars yearly. For all these reasons, in the midst of the current rapid proliferation of this new technology, there is great need for a sensitive and specific method for selecting appropriate TT candidates based on likely beneficial outcome, that can be used in the emergency clinical setting where these decisions are made.

SUMMARY OF THE INVENTION

In general, in one aspect, the invention is an instrument for predicting the benefit of using thrombolytic therapy to treat a patient with a heart condition. The invention includes a first input port for receiving inputs derived from electrocardiograph measurements of the patient's condition, and a processor for computing an estimate of said benefit based upon the electrocardiograph-derived inputs.

Preferred embodiments include the following features. The instrument also includes an electrocardiograph for generating an electrocardiograph waveform relating to the condition of the patient, and a waveform analyzer for analyzing the electrocardiograph waveform and generating the electrocardiograph-derived inputs. The processor computes the benefit by computing a first and a second probability of acute hospital mortality, the first probability being computed under the assumption that no thrombolytic therapy is applied and the second probability being computed under the assumption that thrombolytic therapy is applied. The processor uses an empirically based mathematical model of actual clinical experience to compute the first and second probabilities of acute hospital mortality, in particular, a logistic regression model. The instrument also includes a second input port for receiving inputs relating to basic clinical data for the patient and the processor is adapted to use said clinical data inputs along with said electrocardiograph-derived inputs to compute the estimate of said benefit.

One advantage of the invention is that it can be used in a real-time clinical setting where it can quickly provide a measure of the predicted benefit of using TT that is statistically based upon actual clinical data. When incorporated into a computer-assisted electrocardiograph for EMS (Emergency Medical Service) and ER (Emergency Room) use, the invention will help identify TT candidates at the earliest possible moment.

Furthermore, because the invention uses a multivariate regression model, it can take into account a wider range of relevant patient attributes than could be effectively considered by the unassisted practitioner when evaluating the potential benefit of using TT on a particular patient. Moreover, since the underlying regression models are based upon actual clinical data, they reflect actual clinical experience and can be updated to capture the growing experience of just-completed and currently ongoing trials of TT. Thus, one would expect that the performance of the predictive instrument will improve as more data becomes available to refine the underlying models and the list of explanatory variables used in the models.

Other advantages and features will become apparent from the following description of the preferred embodiment, and the claims.

DESCRIPTION OF THE PREFERRED EMBODIMENT

Figure 1:
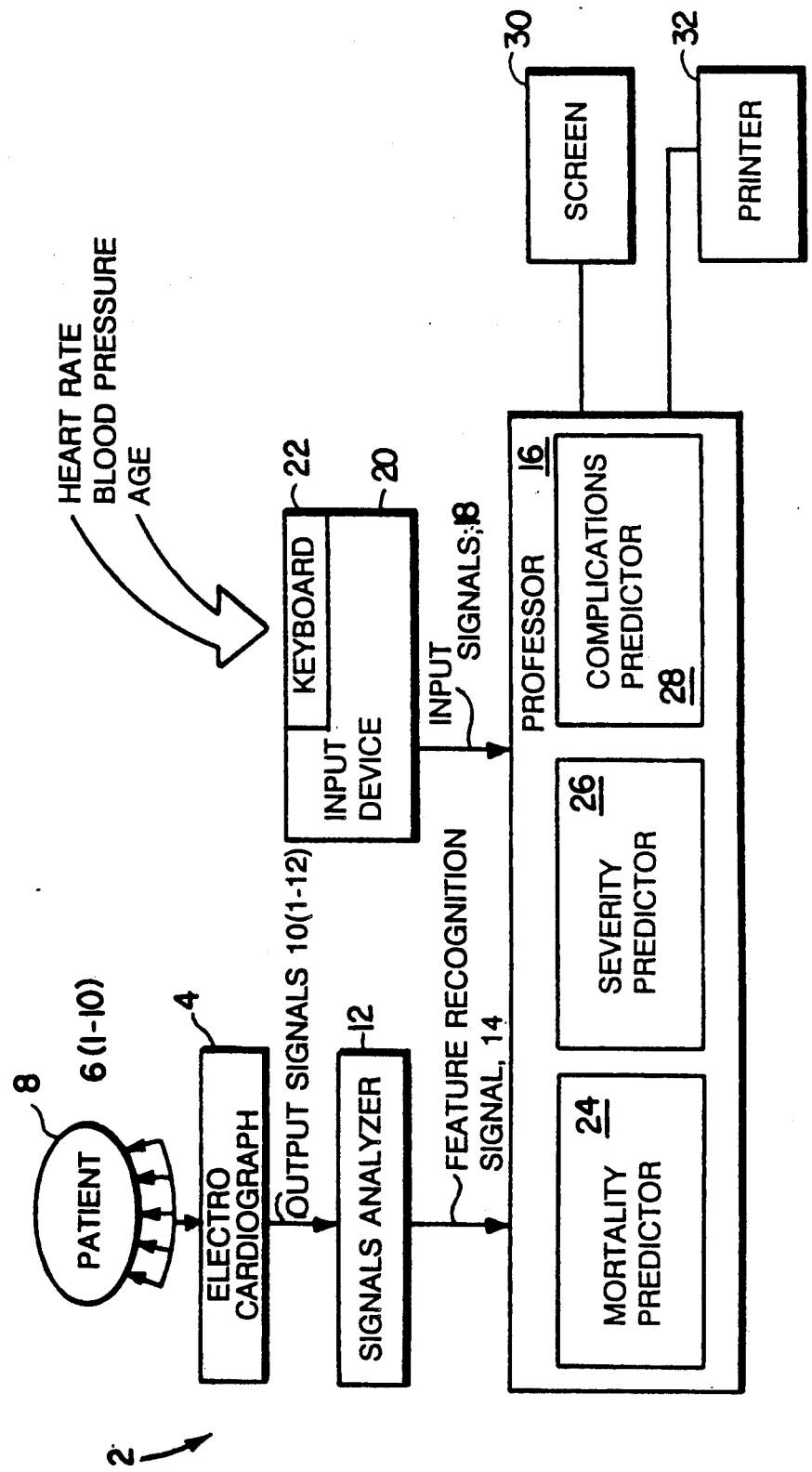
FIG. 1 illustrates a thrombolysis predictive instrument.

FIG. 3 lists the values of the coefficients used in the logistic regression model of FIG. 1.

Referring to FIG. 1, in a thrombolysis predictive instrument (TPI) 2, an electrocardiograph 4 having ten electrodes 6(1–10) monitors the cardiac activity of a patient 8 who has recently experienced an acute myocardial infarction (AMI). Each of the ten electrodes 6 is positioned on patient 6 so as to detect the cardiac activity of a different portion of the patient's heart. Twelve leadbased output signals 10(1–12) are derived from the cardiac activity signals detected by the ten electrodes 6(1–10). A signal analyzer 12, which receives output signals 10(1–12), extracts certain information from them. In particular, signal analyzer 12 searches output signals 10(–12) for the presence or absence of certain critical electrocardiogram (ECG) features (e.g., T wave inversion, presence or absence of Q waves) and it measures the magnitude of other critical features (e.g., ST elevation or depression). Then, signal analyzer 12 digitally encodes the extracted information to generate a feature recognition signal 14, which is sent to a digital processor 16.

Some commercially available computer-assisted electrocardiograph's combine both the electrocardiograph and signal analyzer functions and thus could be used for electrocardiograph 4 and signal analyzer 12. An HP (Hewlett Packard) Pagewriter is one such example. The signal analyzer portion of such equipment can be programmed, using, for example, the ElectroCardiograph Language (ECL) which is also available from HP, to recognize whether the lead-based signals from the electrocardiograph contain particular features. Or, it may be programmed to identify the location of the myocardial infarction (MI) based upon the presence of certain identifiable waveform characteristics.

Besides receiving the output from signal analyzer 12, digital processor 16 also receives an input signal 18 from an input device 20. Input signal 18 carries digitally encoded information including clinical data that was derived from patient 8 (e.g., systolic blood pressure, heart rate, primary location of myocardial infarction (MI), secondary MI location) and including information relating to the patient's medical history (e.g., age, sex, previous history of AMI). Input device 20 includes a keypad 22 through which a physician may enter clinical data and medical history information.

Digital processor 16 is programmed to run three different algorithms, each of which uses some or all of the information which was sent by signal analyzer 12 and input device 20 to predict a consequence of administering thrombolysis therapy (TT) to patient 8. A Mortality Predictor Algorithm (MPA) 24 predicts the expected reduction in the probability of acute hospital mortality due to administering TT. A Severity Predictor Algorithm (SPA) 26 predicts the expected change in the severity of the patient's condition due to administering TT. And, a Complications Predictor Algorithm (CPA) 28 predicts the expected change in the likelihood of complications due to administering TT. The results from each of these algorithms are then visually displayed on a screen 30 and/or as output of a printer 32, both of which are connected to digital processor 16. The models on which each of these algorithms are based will now be described in greater detail.

MPA 24 uses a logistic regression equation to model the predicted benefit of using TT. A generalized form of the equation is as follows:

$$P(T) = 100 [1 + e^{-Z}]^{-1} \quad (Eq. 1)$$

$$Z = b_0 + \Sigma_i b_i X_i + T(C_0 + \Sigma_k c_k Y_k) \quad (Eq. 2)$$

where
P(T) is the probability of acute hospital mortality as a function of T;
T is a variable indicating whether or not TT is administered to the patient, where T=0 indicates not administered and T=1 indicates administered;
$X_i$ for $1 \leq i \leq p$, are p independent clinical variables;
$Y_k$ for $0 \leq k \leq m$, are m independent clinical variables and interaction terms relating to the use of TT;
$b_0$ is an intercept coefficient;
$b_i$ is the coefficient of the $i^{th}$ independent variable $X_i$; and
$c_k$ is the coefficient of the $k^{th}$ variable $Y_k$.

The probability of acute hospital mortality is commonly understood to mean the probability of dying from a current acute condition, generally during the specific initial hospitalization for the problem. That is, it is a short term, as opposed to a long term, probability of mortality which does not necessarily have a precisely defined period of time associated with it.

Figure 2:
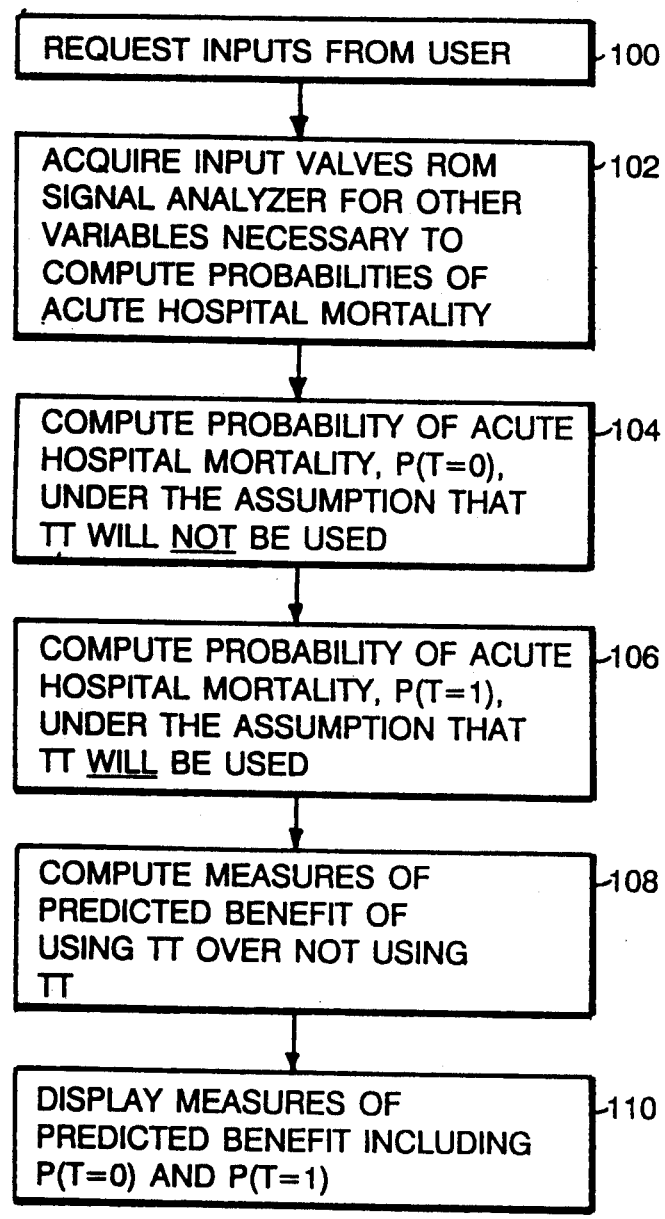
FIG. 2 is the logistic regression model used in the AMI-related mortality predictor of FIG. 1.

Referring to FIG. 2, MPA 24 initially requests the user to input the values for certain clinical variables such as the age and sex of the patient, whether there is a history of MI, blood pressure, pulse rate, etc. (i.e., values for those variables that are not provided by electrocardiograph 4 and signal analyzer 12) (step 100). The request for additional user input is in the form of a menu that is displayed on screen 30 and that lists the variables for which inputs are desired. After the user has entered the required information, MPA 24 acquires other necessary inputs (i.e., the values for the other variables used in Eq. 1) from signal analyzer 12 (step 102). Once MPA 24 has received all of the input values necessary to compute Eq. 1, it then estimates the probability of acute hospital mortality, P(T=0), for the patient under the assumption that no TT will be used (step 104). Then, MPA 24 recomputes a second probability of acute hospital mortality, P(T=1), under the assumption that TT will be used (step 106). In other words, MPA 24 computes Eq. 1 twice, first setting T equal to zero and then setting T equal to one.

After MPA 24 has computed the probabilities of acute hospital mortality, it uses those computed values to generate additional representations of the predicted benefit. More specifically, MPA 24 computes a ratio of P(T=1) to P(T=0) to indicate the relative reduction in the likelihood of mortality (step 108). Then, MPA 24 sends the computed measures of the predicted benefit of using TT to printer 32 and/or to screen 30 where they can be read by the user.

It is believed that both measures of benefit, namely, the probabilities of mortality with and without TT and the computed ratio of those probabilities, are helpful in making a decision on whether to use TT on the patient. Indeed, another useful way of presenting a measure of the benefit of using TT may be as the difference between the two computed probabilities. The ratio and the difference measures reflect relative improvement and the absolute values of the probabilities indicate the base from which those improvements occur.

Standard regression techniques may be employed to identify the explanatory variables, namely, the $X_i$'s and the $Y_k$'s and to determine the values of the coefficients. For a description of such techniques and examples of commercially available computer programs that implement them, see N.C. Cary in SUGI Supplement Library User's Guide, SAS Institute, p. 181–202, 1983, and L. Engelman, "PLR Stepwise Logistic Regression," BMDP Statistical Software, Chap. 14.5, pp. 330–334, BMDP publishers, Westwood, Calif.

Of course, the precise set of explanatory variables that are identified and the predictive ability of the resulting logistic equation generally depends upon the quality of the underlying data that is used to develop the model. Such factors as the size and completeness of the database are often of significant importance. Based upon clinical experience, however, one would expect that the variables which would yield a model having the most explanatory power would be selected from a list that includes at least the following variables: age of the patient, sex of the patient, systolic blood pressure, pulse rate, location and size of MI, electrocardiograph variables that relate to the presence, location and size of the MI, a previous history of MI, time since the onset of symptoms, and the type of TT intervention.

FIG. 3 shows a specific embodiment of equation 1 that was derived from summary data presented in two articles, namely, one article entitled "Long Term Effects of Intravenous Thrombolysis in Acute Myocardial Infarction: Final Report of the GISSI Study", *The Lancet*, Oct. 17, 1987, and a second article entitled "Effectiveness of Intravenous Thrombolytic Treatment in Acute Myocardial Infarction," *The Lancet*, Feb. 22, 1986 (p. 397–402), both by the Grouppo Italiano Per Lo Studio Della Streptochinasi—NASI Nell'infarto Miocardico (GISSI) and both incorporated herein by reference. The coefficients were estimated by using standard maximum likelihood techniques that were available in an SAS statistical software package.

In estimating the coefficients, advantage was taken of the fact that the logistic model assumes that the logarithm of the odds ratio is linear in the original variables. That is, from equation 1, $$ln[p/(1-p)] = Z = b_0 + \Sigma_i b_i X_i + T(c_0 + \Sigma_k c_k Y_k).$$

Thus, if $P_{i1}$ is the probability of acute hospital mortality for $X=1$ and $P_{i0}$ is the probability of acute hospital mortality for $X_i=0$, then:

$$ln\left[\frac{P_{i1}}{(1-P_{i1})} \Big/ \frac{P_{i0}}{(1-P_{i1})}\right] = \log(\text{odds ratio}) = b_i. \quad \text{(Eq. 3)}$$

Of the variables identified in FIG. 3, the values for the S1 and S2 variables (i.e., the variables relating to the location of the MI) are generated by signal analyzer 12. Thus, for example, signal analyzer 12 is programmed to recognize the presence of Q waves among the lead-based signals, to measure the duration of the Q waves and to measure the ST elevations on the lead-based signals to identify the location of the MI. The particular combination of electrocardiograph lead-based waveforms that correspond to the different possible locations of the MI are known to those skilled in the art and must be programmed into the computer-assisted electrocardiograph to be incorporated into the operation of TPI 2. In this case, an anterior MI is indicated by the presence of either a Q wave of duration $\geq 0.03$ seconds and/or an ST elevation $>0.2$ mV in two of leads $V_1$ through $V_6$; while, an inferior MI is indicated by the presence of either a Q wave of duration $\geq 0.03$ seconds and/or an ST elevation $>0.1$ mV in leads II, III and aVF. If the telltale features of an anterior MI are recognized by signal analyzer 12, then it indicates to MPA 24 that the MI is anterior and the value for S1 is set to one for the subsequent computation of the probability of acute mortality.

Referring back to FIG. 1, SPA 26 uses a linear regression equation to model the expected change in the severity of patient's condition as a result of using TT. The specific dependent variable that is computed by the linear regression equation is the cardiac LVEF of the patient. By computing the LVEF for two alternatives, namely, not using TT and using TT, the amount by which the LVEF will be reduced by using TT can be predicted. The linear regression equation is of the form:

$$L(T) = a_0 \Sigma_i a_i X_i + T(d_0 + \Sigma_k d_i Y_k) \quad \text{(Eq. 4)}$$

where

L(T) is the LVEF as a function of T;

T is a variable indicating whether or not TT is administered to the patient, $T=0$ indicates not administered and $T=1$ indicates administered;

$X_i$ for $1 \leq i \leq r$, are r independent clinical variables;

$Y_k$ for $0 \leq k \leq s$, are s independent clinical variables and interaction terms relating to the use of TT;

$a_0$ is an intercept coefficient;

$a_i$ is the coefficient of the $i^{th}$ independent variable $X_i$; and $d_k$ is the coefficient of the $k^{th}$ variable $Y_k$.

It is expected that systolic blood pressure, heart rate and ECG features will prove to be among the most important of the independent variables used in Eq. 4.

As with MPA 24, the inputs for SPA 26 and thus for Eq. 4 are provided by signal analyzer 12 and user input through keypad 22. It is expected that many of the same inputs that are required by MPA 24 will also be used by SPA 26. After the required inputs are available, SPA 26 computes the predicted change in LVEF by computing Eq. 4 twice, once for $T=0$ (i.e., not using TT) and once for $T=1$ (i.e., using TT). The difference between the two results (i.e., $L(T=1) - L(T=0)$) represents the reduction in LVEF and provides a good measure of the increase in the severity of cardiac damage that may result from using TT.

Finally, CPA 28, like MPA 24, uses a logistic regression equation to model the likelihood of an increase in complications resulting from using TT. The underlying logistic regression equation is of the form:

$$C(T) = 100 [1 + e^{-W}]^{-1} \quad \text{(Eq. 5)}$$

$$W = f_0 + \Sigma_i f_i X_i + T(h_0 + \Sigma_k h_k Y_k) \quad \text{(Eq. 6)}$$

where

C(T) is the probability of complications occurring as a function of T;

T is a variable indicating whether or not TT is administered to the patient, $T=0$ indicates not administered and $T=1$ indicates administered;

$X_i$ for $1 \leq i \leq q$, are q independent clinical variables;

$Y_k$ for $0 \leq k \leq n$ are n independent clinical variables and interaction terms relating to the use of TT;

$f_0$ is an intercept coefficient;

$f_i$ is the coefficient of the $i^{th}$ independent variable $X_i$; and $h_k$ is the coefficient of the $k^{th}$ variable $Y_k$.

The complications which are desirable to incorporate into the model include increased likelihood of stroke, major bleeds, minor bleeds, and/or hypotension. For modeling such complications, one would expect that important independent variables would be age, history of any of the following: hypertension, recent surgery, bleeding disorders and stroke.

CPA 28 operates similarly to MPA 24 and SPA 26. That is, CPA 28 computes two estimates of the likelihood of complications, one for $T=0$ and one for $T=1$. Then, CPA 28 calculates the difference and/or ratio of the two computed estimates as a measure of the predicted increase in complications due to using TT. This information is also provided to the user as a further basis upon which to decide whether TT should be used on the patient.

The outputs of the three predictive algorithms, namely, MPA 24, SPA 26 and CPA 28, are sent to printer 32 which then prints them along with the underlying ECG waveforms so that the user has a permanent record of the patient's condition and of the predictions of the consequences of using TT on the patient.

Having thus described illustrative embodiments of the invention, it will be apparent that various alterations, modifications and improvements will readily occur to those skilled in the art. For example, although the regression equations described above were single equations with a term for indicating whether TT was or was not used, separate equations could be used for those two alternatives. Furthermore, other regression models could be employed such as those derived from discriminate analysis or recursive partitioning. In addition, it may be desirable to represent some of the independent variables not as dichotomous variables but rather as continuous linear or even nonlinear variables. For example, age could be represented in quadratic form to reflect the fact older people experience disproportionately more risks to their health from medical intervention than do younger people.

Such alterations, modifications and improvements, and others not expressly described above, are nonetheless intended to be implied and are within the spirit and scope of the invention. Accordingly, the foregoing discussion is intended to be illustrative only, and not limiting. The invention is limited and defined only by the following claims and equivalents thereto.

What is claimed is:

1. An instrument for evaluating whether to use thrombolytic therapy to treat a patient with a heart condition, the instrument comprising:
   a first input means adapted to be coupled to said patient for receiving electrocardiographic data from the patient before using thrombolytic therapy on said patient; and
   a processing means for computing a predicted benefit to the cardiovascular health of the patient as a consequence of using thrombolytic therapy on said patient, said predicted benefit being derived from said electrocardiographic data.

2. The instrument of claim 1 further comprising:
   an electrocardiograph for generating an electrocardiograph waveform for said patient; and
   a waveform analyzer for analyzing the electrocardiograph waveform and generating said electrocardiographic data.

3. The instrument of claim 2 wherein said processing means computes said predicted benefit by computing a first and a second probability of acute hospital mortality, the first probability being computed using an assumption that no thrombolytic therapy is applied and the second probability being computed using an assumption that thrombolytic therapy is applied.

4. The instrument of claim 3 wherein said processing means uses an empirically based mathematical model to compute the first and second probabilities of acute hospital mortality, said model being derived from data about patients to whom thrombolytic therapy was administered.

5. The instrument of claim 4 wherein said processing means uses a regression model to compute the first and second probabilities of acute hospital mortality.

6. The instrument of claim 5 wherein said processing means uses a multivariate logistic regression model to compute the first and second probabilities of acute hospital mortality.

7. The instrument of claim 3 further comprising a second input means for receiving clinical data inputs conveying clinical data about said patient and wherein said processing means is adapted to use said clinical data inputs along with said electrocardiographic data to compute said predicted benefit.

8. The instrument of claim 1 wherein said processing means computes said predicted benefit by computing a first and a second probability of acute hospital mortality, the first probability being computed using an assumption that no thrombolytic therapy is applied and the second probability being computed using an assumption that thrombolytic therapy is applied.

9. The instrument of claim 8 wherein said processing means uses an empirically based mathematical model to compute the first and second probabilities of acute hospital mortality, said model being derived from data about patients to whom thrombolytic therapy was administered.

10. The instrument of claim 9 wherein said processing means uses a regression model to compute the first and second probabilities of acute hospital mortality.

11. The instrument of claim 10 wherein said processing means uses a multivariate logistic regression model to compute the first and second probabilities of acute hospital mortality.

12. The instrument of claim 1 further comprising a second input means for receiving inputs relating to clinical data for the patient and wherein said processing means is adapted to use said clinical data inputs along with said electrocardiographic data to compute said predicted benefit.

13. A method for determining whether to use thrombolytic therapy to treat a patient with a heart condition, the method comprising:
   using an electrocardiograph to measure the patient's condition before using thrombolytic therapy on said patient;
   generating input signals from electrocardiograph measurements of the patient's condition;
   using a processor to estimate a benefit to the cardiovascular health of the patient as a consequence of using thrombolytic therapy on said patient, said estimated benefit being derived from the electrocardiograph-derived inputs; and
   using the estimated benefit to decide whether to apply thrombolytic therapy to said patient.

14. The method of claim 13 wherein the step of using an electrocardiograph comprises generating an electrocardiograph waveform for said patient, and wherein the method further comprises using a waveform analyzer to generate the electrocardiograph-derived inputs from the electrocardiograph waveform.

15. The method of claim 13 wherein the processor estimates the benefit by computing a first and a second probability of acute hospital mortality, the first probability being computed using an assumption that no thrombolytic therapy is applied and the second probability being computed using an assumption that thrombolytic therapy is applied.

16. The method of claim 15 wherein the processor uses an empirically based mathematical model to compute the first and second probabilities of acute hospital mortality, said model being derived from data about patients to whom thrombolytic therapy was administered.

17. The method of claim 16 wherein the processor uses a regression model to compute the first and second probabilities of acute hospital mortality.

18. The method of claim 17 wherein the processor uses a multivariate logistic regression model to compute the first and second probabilities of acute hospital mortality.

19. The method of claim 13 further comprising supplying clinical data for the patient to the processor and wherein the processor is adapted to use said clinical data along with said electrocardiograph-derived inputs to estimate said benefit.

* * * * *

UNITED STATES PATENT AND TRADEMARK OFFICE
CERTIFICATE OF CORRECTION

PATENT NO. : 4,998,535

DATED : March 12, 1991

INVENTOR(S) : Harry P. Selker et al.

It is certified that error appears in the above-identified patent and that said Letters Patent is hereby corrected as shown below:

Col. 2, line 64; "10(-12)" should be --10(1-12)--

Col. 3, line 50; add --)-- after "Yk"

Col. 5, line 25; "X = 1" should be --$X_i = 1$-- line 66; "$a_0 \Sigma_i a_i X_i$" should be --$a_0 + \Sigma_i a_i X_i$--

Signed and Sealed this

Twenty-ninth Day of September, 1992

Attest:

DOUGLAS B. COMER

*Attesting Officer*  *Acting Commissioner of Patents and Trademarks*